(12) United States Patent
Litvin

(10) Patent No.: US 10,307,292 B2
(45) Date of Patent: Jun. 4, 2019

(54) DEVICE FOR ADJUSTING THE INTRAOCULAR PRESSURE

(75) Inventor: Gilad Litvin, Moshav Sde Varburg (IL)

(73) Assignee: MOR RESEARCH APPLICATIONS LTD, Petach Tikva (IL)

( * ) Notice: Subject to any disclaimer, the term of this patent is extended or adjusted under 35 U.S.C. 154(b) by 211 days.

(21) Appl. No.: 14/233,614

(22) PCT Filed: Jul. 18, 2012

(86) PCT No.: PCT/IL2012/050256
§ 371 (c)(1),
(2), (4) Date: Jan. 17, 2014

(87) PCT Pub. No.: WO2013/011511
PCT Pub. Date: Jan. 24, 2013

(65) Prior Publication Data
US 2014/0148752 A1    May 29, 2014

Related U.S. Application Data

(60) Provisional application No. 61/508,792, filed on Jul. 18, 2011.

(51) Int. Cl.
*A61M 5/00* (2006.01)
*A61F 9/007* (2006.01)
(Continued)

(52) U.S. Cl.
CPC ........ *A61F 9/00781* (2013.01); *A61F 9/0017* (2013.01); *A61F 13/15252* (2013.01);
(Continued)

(58) Field of Classification Search
CPC ............ A61F 13/0017; A61F 13/15252; A61F 9/0008; A61F 9/00781; A61F 2009/00891;
(Continued)

(56) References Cited

U.S. PATENT DOCUMENTS 3,737,508 A    6/1973   Weir
3,950,478 A    4/1976   Kenworthy et al.
(Continued)

FOREIGN PATENT DOCUMENTS

EP    0 487 418 A1    5/1992
EP    0 937 443 A2    8/1999
(Continued)

OTHER PUBLICATIONS

Hansen et al. (Water absorption and mechanical properties of electrospun structured hydrogels. Appl. Polym. Sci. 2005, 95, 427-434).*
(Continued)

*Primary Examiner* — Ariana Zimbouski
(74) *Attorney, Agent, or Firm* — Pearl Cohen Zedek Latzer Baratz LLP; Mark Cohen

(57) ABSTRACT

Provided is a device for use in controlling the liquid outflow from the anterior chamber of the eye, methods of draining aqueous humor from the anterior chamber to the intra-orbital space using the device, methods for controlling the liquid outflow from the anterior chamber of the eye and further surgical methods for implanting the presently described device.

19 Claims, 2 Drawing Sheets

(51) Int. Cl.
  *A61L 31/04* (2006.01)
  *A61L 31/14* (2006.01)
  *A61L 31/16* (2006.01)
  *A61F 9/00* (2006.01)
  *A61F 13/15* (2006.01)
  *A61M 27/00* (2006.01)

(52) U.S. Cl.
  CPC ............. *A61L 31/04* (2013.01); *A61L 31/146* (2013.01); *A61L 31/16* (2013.01); *A61M 27/002* (2013.01)

(58) Field of Classification Search
  CPC ...... A61F 9/0017; A61L 31/04; A61L 31/146; A61L 31/16; A61M 27/002
  See application file for complete search history.

(56) References Cited

U.S. PATENT DOCUMENTS

| | | |
|---|---|---|
| 3,996,321 A | 12/1976 | Weinberger |
| 4,014,335 A * | 3/1977 | Arnold .................. A61F 9/0017 424/427 |
| 4,189,336 A | 2/1980 | Hutflesz |
| 4,402,900 A | 9/1983 | Berry, Jr. |
| 4,421,707 A | 12/1983 | Kourtz et al. |
| 4,431,602 A | 2/1984 | Behrens et al. |
| 4,554,918 A | 11/1985 | White |
| 4,557,732 A | 12/1985 | Hähnke et al. |
| 4,643,657 A | 2/1987 | Achelpohl et al. |
| 4,781,675 A * | 11/1988 | White .................. A61F 9/0017 604/10 |
| 4,804,511 A | 2/1989 | Pieper et al. |
| 4,946,436 A | 8/1990 | Smith |
| 5,002,474 A | 3/1991 | Hoekstra |
| 5,005,577 A | 4/1991 | Frenkel |
| 5,032,020 A | 7/1991 | Robert |
| 5,071,408 A | 12/1991 | Ahmed |
| 5,122,329 A | 6/1992 | Mort et al. |
| 5,147,393 A | 9/1992 | Van Noy et al. |
| 5,171,213 A | 12/1992 | Price, Jr. |
| 5,190,553 A | 3/1993 | Kanert et al. |
| 5,300,020 A * | 4/1994 | L'Esperance, Jr. .......................... A61F 9/00781 604/9 |
| 5,372,577 A | 12/1994 | Ungerleider |
| 5,387,387 A | 2/1995 | James et al. |
| 5,490,938 A | 2/1996 | Sawan et al. |
| 5,520,631 A | 5/1996 | Nordquist et al. |
| 5,626,558 A | 5/1997 | Suson |
| 5,667,743 A | 9/1997 | Tai et al. |
| 5,713,844 A | 2/1998 | Peyman |
| 5,743,868 A | 4/1998 | Brown et al. |
| 5,876,440 A | 3/1999 | Feingold |
| 6,054,122 A | 4/2000 | MacPhee et al. |
| 6,077,299 A | 6/2000 | Adelberg et al. |
| 6,083,257 A | 7/2000 | Taylor et al. |
| 6,102,939 A | 8/2000 | Pinchuk |
| 6,248,273 B1 | 6/2001 | Benin et al. |
| 6,252,031 B1 | 6/2001 | Tsutsumi et al. |
| 6,280,449 B1 | 8/2001 | Blake |
| 6,390,989 B1 | 5/2002 | Denninghoff |
| 6,443,893 B1 | 9/2002 | Schnakenberg et al. |
| 6,595,945 B2 | 7/2003 | Brown |
| 6,666,841 B2 | 12/2003 | Gharib et al. |
| 6,730,123 B1 | 5/2004 | Klopotek |
| 6,796,942 B1 | 9/2004 | Kreiner et al. |
| 7,130,693 B1 | 10/2006 | Montalbo |
| 7,306,621 B1 | 12/2007 | Halla et al. |
| 7,831,309 B1 | 11/2010 | Humayun et al. |
| 2001/0000527 A1 | 4/2001 | Yaron et al. |
| 2001/0041870 A1 | 11/2001 | Gillis et al. |
| 2001/0047205 A1 * | 11/2001 | Garonzik .................. A61F 2/141 623/6.64 |
| 2002/0002404 A1 | 1/2002 | Sarfarazi |
| 2002/0013545 A1 | 1/2002 | Soltanpour et al. |
| 2002/0013572 A1 | 1/2002 | Berlin |
| 2002/0026200 A1 | 2/2002 | Savage |
| 2002/0052544 A1 | 5/2002 | Jeffries et al. |
| 2002/0087111 A1 | 7/2002 | Ethier et al. |
| 2002/0099359 A1 | 7/2002 | Santini, Jr. et al. |
| 2002/0107567 A1 | 8/2002 | Terwee et al. |
| 2002/0127250 A1 | 9/2002 | Guo et al. |
| 2002/0143284 A1 | 10/2002 | Tu et al. |
| 2002/0161437 A1 | 10/2002 | Zhou et al. |
| 2002/0167735 A1 | 11/2002 | Jethmalani et al. |
| 2002/0177856 A1 | 11/2002 | Richter et al. |
| 2002/0188308 A1 | 12/2002 | Tu et al. |
| 2002/0193725 A1 | 12/2002 | Odrich |
| 2003/0057347 A1 | 3/2003 | Weiss |
| 2003/0167893 A1 | 4/2003 | Miller et al. |
| 2003/0078487 A1 | 4/2003 | Jeffries et al. |
| 2003/0087845 A1 | 5/2003 | Nyce |
| 2003/0095995 A1 | 5/2003 | Wong et al. |
| 2003/0120264 A1 | 6/2003 | Lattouf |
| 2003/0147046 A1 | 8/2003 | Shadduck |
| 2003/0175849 A1 | 9/2003 | Schwartz et al. |
| 2003/0176892 A1 | 9/2003 | Shalev |
| 2003/0181353 A1 | 9/2003 | Nyce |
| 2003/0202935 A1 | 10/2003 | Nyce |
| 2003/0212383 A1 | 11/2003 | Cote et al. |
| 2003/0216329 A1 | 11/2003 | Robinson et al. |
| 2003/0220603 A1 | 11/2003 | Lynch et al. |
| 2003/0220660 A1 * | 11/2003 | Kortenbach ........ A61B 17/0643 606/151 |
| 2003/0224032 A1 | 12/2003 | Read et al. |
| 2003/0225318 A1 | 12/2003 | Montegrande et al. |
| 2003/0229263 A1 | 12/2003 | Connors et al. |
| 2004/0024453 A1 | 2/2004 | Castillejos |
| 2004/0049022 A1 | 3/2004 | Nyce et al. |
| 2004/0087963 A1 | 5/2004 | Ossipov et al. |
| 2004/0092470 A1 | 5/2004 | Leonard et al. |
| 2004/0098123 A1 | 5/2004 | Freeman et al. |
| 2004/0116794 A1 | 6/2004 | Fink et al. |
| 2004/0127843 A1 | 7/2004 | Tu et al. |
| 2004/0193095 A1 | 9/2004 | Shadduck |
| 2004/0215126 A1 | 10/2004 | Ahmed |
| 2004/0225250 A1 | 11/2004 | Yablonski |
| 2005/0013151 A1 | 1/2005 | Nathanson et al. |
| 2005/0033420 A1 | 2/2005 | Christie et al. |
| 2005/0063996 A1 | 3/2005 | Peyman |
| 2005/0090806 A1 | 4/2005 | Lynch et al. |
| 2005/0090807 A1 | 4/2005 | Lynch et al. |
| 2005/0119636 A1 | 6/2005 | Haffner et al. |
| 2005/0119737 A1 * | 6/2005 | Bene .................. A61F 9/00781 623/4.1 |
| 2005/0143817 A1 | 6/2005 | Hunter et al. |
| 2005/0152946 A1 | 7/2005 | Hunter et al. |
| 2005/0184003 A1 | 8/2005 | Rodgers et al. |
| 2005/0187623 A1 | 8/2005 | Tassignon |
| 2005/0208095 A1 | 9/2005 | Hunter et al. |
| 2005/0226814 A1 | 10/2005 | Levy |
| 2005/0228120 A1 | 10/2005 | Hughes et al. |
| 2005/0242325 A1 | 11/2005 | Mather et al. |
| 2005/0244472 A1 | 11/2005 | Hughes et al. |
| 2005/0261624 A1 | 11/2005 | Wilcox |
| 2005/0271809 A1 | 12/2005 | Kobrin et al. |
| 2005/0273033 A1 | 12/2005 | Grahn et al. |
| 2005/0277802 A1 | 12/2005 | Larsen et al. |
| 2005/0282997 A1 | 12/2005 | Ward et al. |
| 2005/0283108 A1 | 12/2005 | Savage |
| 2005/0288619 A1 * | 12/2005 | Gharib ................ A61F 9/00781 604/8 |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064161 A1 | 3/2006 | Blake |
| 2006/0068031 A1 | 3/2006 | Miller et al. |
| 2006/0074487 A1 | 4/2006 | Gilg |
| 2006/0084907 A1 | 4/2006 | Bergheim et al. |
| 2006/0100288 A1 | 5/2006 | Bague et al. |
| 2006/0116404 A1 | 6/2006 | Robinson et al. |
| 2006/0119793 A1 | 6/2006 | Hillis et al. |
| 2006/0122143 A1 | 6/2006 | Boyer et al. |

(56) References Cited

U.S. PATENT DOCUMENTS

| | | |
|---|---|---|
| 2006/0129129 A1 | 6/2006 | Smith |
| 2006/0136055 A1 | 6/2006 | Michel |
| 2006/0189915 A1 | 8/2006 | Camras et al. |
| 2006/0195055 A1 | 8/2006 | Bergheim et al. |
| 2006/0195056 A1 | 8/2006 | Bergheim et al. |
| 2006/0229265 A1 | 10/2006 | Milburn et al. |
| 2007/0014760 A1 | 1/2007 | Peyman |
| 2007/0112292 A1 | 5/2007 | Tu et al. |
| 2007/0122540 A1 | 5/2007 | Salamone et al. |
| 2007/0142376 A1 | 6/2007 | Fleenor et al. |
| 2007/0156079 A1* | 7/2007 | Brown ............... A61B 3/16 604/9 |
| 2007/0191863 A1 | 8/2007 | De Juan, Jr. et al. |
| 2007/0198083 A1 | 8/2007 | Sel et al. |
| 2007/0207186 A1* | 9/2007 | Scanlon ............ A61F 2/07 424/424 |
| 2007/0208134 A1 | 9/2007 | Hunter et al. |
| 2007/0244560 A1 | 10/2007 | Ossipov et al. |
| 2007/0292474 A1* | 12/2007 | Hsu ............... A61L 27/20 424/427 |
| 2007/0293807 A1 | 12/2007 | Lynch et al. |
| 2007/0298068 A1 | 12/2007 | Badawi et al. |
| 2008/0027304 A1 | 1/2008 | Pardo et al. |
| 2008/0033501 A1 | 2/2008 | Gross |
| 2008/0045878 A1 | 2/2008 | Bergheim et al. |
| 2008/0051681 A1 | 2/2008 | Schwartz |
| 2008/0089480 A1 | 4/2008 | Gertner |
| 2008/0108933 A1 | 5/2008 | Yu et al. |
| 2008/0138375 A1 | 6/2008 | Yan et al. |
| 2008/0156002 A1 | 7/2008 | Willis et al. |
| 2008/0160064 A1 | 7/2008 | Capelli et al. |
| 2008/0228127 A1 | 9/2008 | Burns et al. |
| 2008/0260797 A1 | 10/2008 | Oh-Lee et al. |
| 2008/0319549 A1 | 12/2008 | Greenhalgh et al. |
| 2009/0104243 A1* | 4/2009 | Utkhede ............ A61F 9/0017 424/423 |
| 2009/0124955 A1 | 5/2009 | Ayyala |
| 2009/0137993 A1 | 5/2009 | Kurtz |
| 2009/0182206 A1 | 7/2009 | Najafi et al. |
| 2009/0182421 A1* | 7/2009 | Silvestrini ......... A61F 9/00781 623/6.13 |
| 2009/0227933 A1* | 9/2009 | Karageozian ....... A61F 9/0017 604/8 |
| 2009/0240324 A1* | 9/2009 | Smith ............... A61F 2/86 623/1.42 |
| 2009/0258048 A1 | 10/2009 | Ward et al. |
| 2009/0264428 A1 | 10/2009 | Baldwin et al. |
| 2009/0275924 A1 | 11/2009 | Lattanzio et al. |
| 2009/0280153 A1 | 11/2009 | Hunter et al. |
| 2010/0010414 A1 | 1/2010 | Bergheim et al. |
| 2010/0030225 A1 | 2/2010 | Ianchulev |
| 2010/0074934 A1* | 3/2010 | Hunter ............. A61F 2/16 424/422 |
| 2010/0086579 A1 | 4/2010 | Yan et al. |
| 2010/0094164 A1 | 4/2010 | Chronis |
| 2010/0106073 A1 | 4/2010 | Haffner et al. |
| 2010/0161004 A1 | 6/2010 | Najafi et al. |
| 2010/0174272 A1 | 7/2010 | Weiner |
| 2010/0179284 A1 | 7/2010 | Ward et al. |
| 2010/0203155 A1* | 8/2010 | Wei ............... A61F 2/4603 424/549 |
| 2010/0239637 A1 | 9/2010 | Ciolino et al. |
| 2010/0241046 A1 | 9/2010 | Pinchuk et al. |
| 2010/0272780 A1 | 10/2010 | Ling et al. |
| 2010/0280349 A1 | 11/2010 | Dacquay et al. |
| 2010/0286498 A1 | 11/2010 | Dacquay et al. |
| 2010/0310637 A1 | 12/2010 | Abdulrazik |
| 2010/0331975 A1 | 12/2010 | Nissan et al. |
| 2011/0015644 A1 | 1/2011 | Pankin et al. |
| 2011/0022118 A1 | 1/2011 | Rickard |
| 2011/0046728 A1 | 2/2011 | Shareef et al. |

FOREIGN PATENT DOCUMENTS

| | | |
|---|---|---|
| EP | 1 438 929 A1 | 7/2004 |
| EP | 1 576 941 A1 | 9/2005 |
| WO | 94/13234 A1 | 6/1994 |
| WO | 01/97727 A1 | 12/2001 |
| WO | 02/49535 A2 | 6/2002 |
| WO | 02/49536 A2 | 6/2002 |
| WO | 02/49678 A2 | 6/2002 |
| WO | 02/074189 A2 | 9/2002 |
| WO | 02/074190 A2 | 9/2002 |
| WO | 02/074191 A2 | 9/2002 |
| WO | 03/015667 A1 | 2/2003 |
| WO | 2004/066979 A2 | 8/2004 |
| WO | 2004/066980 A2 | 8/2004 |
| WO | 2005/032400 A2 | 4/2005 |
| WO | 2005/051316 A2 | 6/2005 |
| WO | 2005/065578 A2 | 7/2005 |
| WO | 2006/032763 A2 | 3/2006 |
| WO | 2006/036715 A2 | 4/2006 |
| WO | 2008/030951 A2 | 3/2008 |
| WO | 2009/105573 A1 | 8/2009 |
| WO | 2009/114010 A1 | 9/2009 |
| WO | 2010/001325 A2 | 1/2010 |
| WO | 2010/086849 A1 | 8/2010 |
| WO | 2010/097800 A1 | 9/2010 |
| WO | 2010/100651 A2 | 9/2010 |
| WO | 2010/131032 A2 | 11/2010 |
| WO | 2010/135369 A1 | 11/2010 |
| WO | 2011/008896 A2 | 1/2011 |

OTHER PUBLICATIONS

Hummel (Swelling of cellulose: Puu-23.6080—Cellulose Chemistry, 2016, slide 11).*

El Seoud et al. (Cellulose 2008, 15, Table 3). (provided on slide 11 of Hummel).*

International Search Report for International Application No. PCT/IL2012/050256, four pages, dated Oct. 25, 2012.

Gokharman D. and Aydin S., Magnetic Resonance Imaging in Orbital Pathologies: A Pictorial Review, Journal of the Belgian Society of Radiology. 2018; 102(1); 5, pp. 1-8.

Supplementary European Search Report; completed Feb. 11, 2015, two pages.

* cited by examiner

DEVICE FOR ADJUSTING THE INTRAOCULAR PRESSURE

FIELD OF THE INVENTION

This invention relates to an implantable device for adjusting the intraocular pressure, capable of relieving symptoms and/or treating conditions associated with and related to glaucoma.

BACKGROUND OF THE INVENTION

Glaucoma is an optic neuropathy characterized by acquired atrophy of the optic nerve and loss of retinal ganglion cells and their axons. Among other factors, elevated intraocular pressure contributes to progressive irreversible optic nerve damage and visual field loss, which may lead to complete blindness.

Worldwide, glaucoma is the second leading cause of blindness. Glaucoma affects 1 in 200 people aged fifty and younger, and 1 in 10 over the age of eighty. If the condition is detected early enough it is possible to stop the development or at least slow the progression of glaucoma with medical and surgical means.

Glaucoma is associated with increased pressure (intraocular pressure) of the liquid (aqueous humor) in the anterior chamber of the eye. There are many different sub-types of glaucoma but they can all be considered a type of optic neuropathy. Raised intraocular pressure is a significant risk factor for developing glaucoma (above 21 mmHg or 2.8 kPa). It is noted that nerve damage may develop due to increase in the intraocular pressure, however the magnitude of increased pressure that may cause nerve damage is individual, i.e. for certain people a relatively small increase in the intraocular pressure may result in irreversible nerve damage, while other people may have high eye pressure for long periods of time (i.e. months or years) before developing nerve damage. Untreated glaucoma leads to permanent damage of the optic nerve fibers and progressive visual field loss, which can lead to complete blindness.

Glaucoma can be divided roughly into two main categories, "open angle" glaucoma (OAG) and "closed angle" glaucoma (CAG). CAG can appear suddenly, leading to excruciating pain, or insidiously with minimal discomfort. In the acute form visual loss can progress quickly but the discomfort often leads patients to seek medical attention before permanent damage occurs. OAG and chronic angle closure glaucoma tends to progress at a slower rate and the patient may not notice that they have lost vision until the disease has progressed significantly.

The intraocular pressure is maintained by the dynamic equilibrium of aqueous production and outflow. The iris divides the anterior portion of the eye into anterior and posterior chambers, which communicate through the pupil. Aqueous humor, produced by the ciliary body, fills the posterior chamber, flows through the pupil into the anterior chamber, and leaves the eye through the trabecular meshwork, a connective tissue filter at the angle between the iris and the cornea. The aqueous humour passes through the trabecular meshwork into Schlemm's canal and into the episcleral venous system. Increased intraocular pressure is caused by obstruction to outflow. In OAG conditions, obstruction exists at a microscopic level in the trabecular meshwork. In CAG the iris obstructs the trabecular meshwork physically either because of anatomic variation leadingto pupillary block and obstruction of aqueous humor flow into the anterior chamber, or by formation of adhesions between the iris and trabeculum.

There are a number of known devices intended to control the intraocular pressure in glaucomatotic eyes:

U.S. Pat. No. 5,300,020 discloses a surgically implantable device for controlled drainage flow of aqueous fluid from the anterior chamber of the eye into nearby sub-conjunctival space, for the relief of a glaucomatous condition of excessive pressure within the eye. The porous material in the device of U.S. Pat. No. 5,300,020 is indicated to be biodegradable, thus within a matter of time this material is decomposed, leaving a hollow tube connecting the anterior chamber with the near sub-conjunctival space. The purpose and effect of the biodegradability of the porous material inside the device is to avoid early hypotony. However, this device will not be able to improve surgical outcome since draining fluid to the near subconjuctival space will be able to relieve intraocular pressure for a short period of time. With time scar tissue will develop in a percentage of patients thus clogging the device and conjunctival bleb.

U.S. Pat. No. 5,743,868 discloses a unitary, pressure-regulating corneal implant device for use in controlling intraocular pressure. This implant, having a conduit with a bore and a porous core material disposed in the bore, allows egress of aqueous humor from the anterior chamber of the eye. The conduit is elongated for extending from the ocular surface of the eye substantially flush therewith through the corneal stroma, and into the anterior chamber. This is an open system device, thus allowing egress of fluid into the eye possibly containing infections agents. Cornea will most probably reject the device as a foreign body (usually the case when implanting a body into the cornea) and also distorts the optical surface of the cornea thereby giving rise to optical aberations to patients treated with this device.

U.S. Pat. No. 4,946,436 relates to a porous device for implantation in the scleral tissue of the eye to relieve the intraocular pressure of glaucoma and a method for surgically implanting the device. It is noted that such devices are intended for being implanted intrasclerally and thus will be able to remove the fluid only to the subsidiary space. Devices described in U.S. Pat. No. 4,946,436 were not found to improve surgical results when compared with trabeculectomy, where treating glaucoma.

SUMMARY OF THE INVENTION

The invention provides a device comprising at least one type of porous, swellable polymeric fibrous material, for use in controlling the liquid outflow from the anterior chamber of the eye.

In a further aspect the invention provides a surgical method for implanting a device of the invention, thus locating said device into an eye of a subject suffering from abnormal liquid pressure at the anterior chamber of the eye, thereby controlling liquid outflow from the anterior chamber of the eye. Thus, upon surgically inserting said device of the invention using a method of the invention, certain symptoms or conditions of glaucoma may be ameliorated, relived or at least reduced.

It is to be noted that the control of liquid outflow from the anterior chamber of the eye is achieved using a device of the invention, implanted by a method of the invention, is capable of adjusting the intraocular pressure. Furthermore, the adjustment of intraocular pressure using the device of the invention is suitable for treating glaucoma condition in the eye of a subject suffering therefrom.

The invention further provides a device comprising a tubular portion having a first and second opening, being implanted so that first opening is located inside the anterior chamber and the second opening is located at the intra-orbital space and said tubular portion is located on the sclera.

In a further aspect the invention provides a method of draining aqueous humor from the anterior chamber to the intra-orbital space comprising the step of implanting a device comprising a tubular portion having a first and second opening; wherein said first opening is located in the anterior chamber and second opening is located at the intra-orbital space and said tubular portion is located on the sclera.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
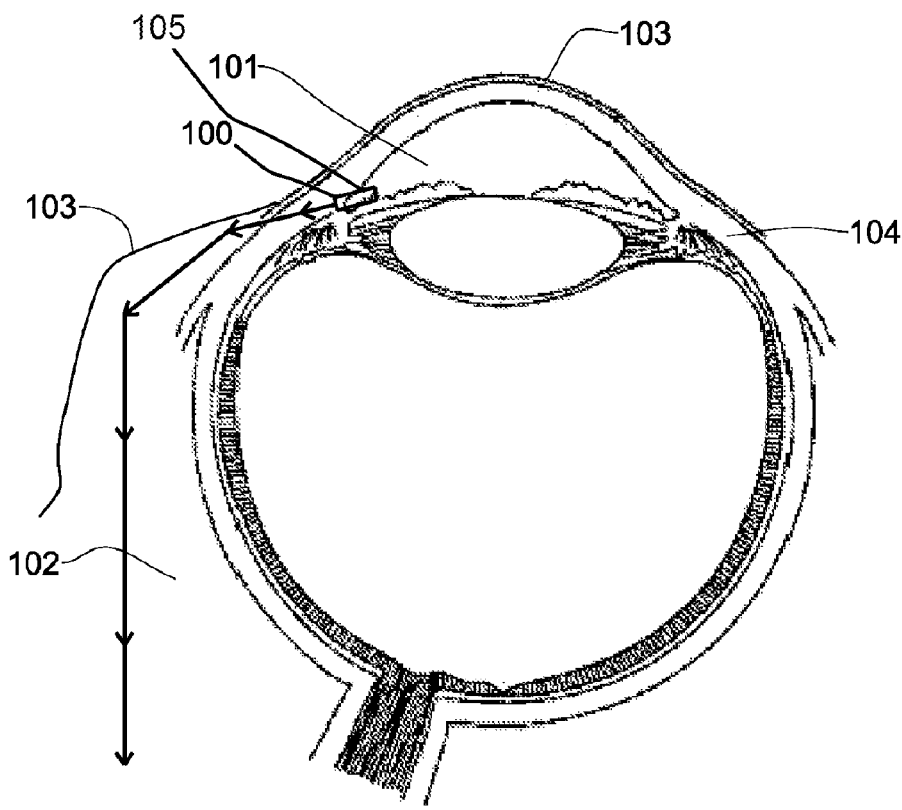
FIG. 1 represents a schematic illustration of the eyeball in a transverse plane through the eyeball, wherein the location of the device of the invention upon its implanting is indicated.

According to the main aspect of the invention there is provided a device comprising at least one type of porous and/or swellable polymeric fibrous material, for use in controlling the liquid outflow from the anterior chamber of the eye.

Under some embodiments of the device of the invention, control of liquid outflow from the anterior chamber of the eye is capable of adjusting the intraocular pressure. Under further embodiments the adjustment of intraocular pressure using the device of the invention is suitable for treating glaucoma condition in the eye of a subject suffering therefrom.

When referring to a "porous, swellable polymeric fibrous material" it should be understood to encompass any type of polymeric fibrous (i.e. plurality of fibers characterized by a high ratio of length-to-width ratios, typical in the order of 1000 to 1) material having pores (predetermined degree of porosity), that upon contact with a liquid is capable of adsorbing a volume of said liquid, thereby gradually expending its physical volume and/or its pore size. Beyond a predetermined swellability volume of said polymeric fibrous material, at least a part of liquid coming in contact with said polymeric fibrous material flows through it. Said fibrous material can be spun into a yarn or made into a fabric by interlacing (weaving), interlooping (knitting), or interlocking (bonding).

The terms "polymer" or "polymeric" (or any of its lingual diversities) as used herein is meant to encompass any type of polymer, including but is not limited to, homopolymer, copolymer, e.g., block, graft, random and alternating copolymer, terpolymer, etc., and blends and/or modifications thereof. Furthermore, unless otherwise specifically limited, the term "polymer" includes all possible geometrical configurations, including, without limitation, isotactic, syndiotactic and atactic symmetries.

In various exemplary embodiments of the invention the porous, swellable polymeric fibrous material is capable of absorbing or adsorbing at least about 3 times its weight and, more desirably, at least about 6 times its weight in the presence of said fluid.

In some embodiments, said porous, swellable polymeric fibrous material can be a natural, synthetic or semi-synthetic polymer. In further embodiments, said porous, swellable polymeric fibrous material can be an inorganic polymer, or an organic polymer.

Representative examples of porous, swellable polymeric fibrous material suitable for the present invention, include, without limitation, modified polyurethanes such as those marketed under the trade names, Hydrothane™, Hydromed™ and Hydroslip™, polyacrylamide, polyvinyl alcohol, poly (hydroxyethyl methacrylate), poly (hydroxypropyl methacrylate), polyacrylate-polyalcohol and the like.

In some embodiments, said porous, swellable polymeric fibrous material may also comprise other materials, such as, but not limited to, poly (isobutylene-co-maleic acid) sodium salt, gelatin and collagen. In various exemplary embodiments of the invention the outer surface of said porous, swellable polymeric fibrous material is enveloped (covering at least a portion of said porous, swellable polymeric fibrous material) with at least one other type of polymeric material. In some embodiments said enveloping polymer is a biocompatible polymer. In other embodiments, said enveloping polymer is a biodegradable polymer. In further embodiments said enveloping polymer is another type of porous, swellable polymeric fibrous material. In some further embodiments, said enveloping polymer is selected from a group consisting of polysaccharide, gelatin and/or hydroxypropyl methyl cellulose (HPMC).

In additional embodiments, said device of the invention may further comprise biostable and/or biodegradable polymer fibers for increasing its hydrophility. Representative examples of suitable biostable polymers include, without limitation, thermoplastic polyurethane, polydimethylsiloxane or another type of silicone rubber, polyester, polyolefin, polymethylmethacrylate, vinyl halide polymer and copolymer, polyvinyl aromatic, polyvinyl ester, polyamide, polyimide and polyether. Representative examples of suitable biodegradable polymers, include, without limitation, poly (L-lactic acid), poly (lactide-co-glycolide), polycaprolactone, polyphosphate ester, poly (hydroxy-butyrate), poly (glycolic acid), poly (DL-lactic acid), poly (amino acid), cyanocrylate, and biolmolecules such as collagen, DNA, silk, chitozan and cellulose derivatives.

When referring to the "control of liquid outflow from the anterior chamber of the eye" it should be understood to include any degree of influence on the outflow of liquid from the anterior chamber of the eye, thereby enabling the drainage of said liquid to an exterior part of the eye, such as for example to the intraorbital space. Outflow in normal, healthy eyes ranges thru 0.22-0.3 µL/min/mm Hg. In glaucoma the drainage angle is compromised having outflow facility usually below 0.10 µL/min/mm Hg. The current invention aims to supply facility at least equivalent to normal/non glaucomatous eyes.

In some embodiments of a device of the invention, said porous swellable polymeric fibrous material is non-woven.

When referring to "non-woven material" it should be understood to encompass any material (including fabric-like material, felt, sheet or web structures) made from long fibers, bonded/entangling together by chemical, mechanical, heat or solvent treatment, which are neither woven nor knitted. Such materials are typically made directly from separate fibers or from molten polymers. They are not made by weaving or knitting and do not require converting the fibers to yarn. Typical non-woven processes include electrospinning, electrospraying, solution dry spinning, staple-laying, spun-laying, air-laying, wet-laying, and so forth. In some case a further bonding step is required.

In other embodiments of a device of the invention, said porous swellable polymeric fibrous material is electrospun.

The term "electrospinning" or "electrospun" or any of its lingual deviations should be understood to encompass a process using an electrical charge to draw very fine (typically on the micro or nano scale) fibers from a liquid. Electrospinning from molten precursors is also practiced; this method ensures that no solvent can be carried over into the final product. The fibers produced using electrospinning processes have increased surface area to volume ratio. Various factors are known to affect electrospun fibers include, but are not limited to: solution viscosity, surface tension, electric field intensity and distance.

In a typical electrospinning process a sufficiently high voltage is applied to a liquid droplet of a polymeric material (a polymer solution, a monomeric precursor thereof, sol-gel precursior, particulate suspension or melt), the body of the liquid becomes charged, and electrostatic repulsion counteracts the surface tension and droplet is stretched, at a critical point a stream of liquid erupts from the surface. If the molecular cohesion of the liquid is sufficiently high, stream breakup does not occur (if it does, droplets are electrosprayed) and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber that results from this bending instability leads to the formation of uniform fibers with nanometer-scale diameters.

Biocompatible polymers which may be applied in an electrospinning process include but are not limited to poly (DTE carbonate) polycaprolactone (PCL), polylactic acid (PLA), poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly (vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyvinyl chloride (PVC), hyaluronic acid (HA), chitosan, alginate, polyhydroxybuyrate and its copolymers, Nylon 11, Cellulose acetate, hydroxyappetite, or any combination thereof. Biodegradable and biocompatible polymers include but are not limited to poly(3-hydroxybutyric acid-co-3-hydroxyvaleric acid), poly(DL-lactide), polycaprolactone, and poly(L-lactide) or any combination thereof.

Electrospun fibers are typically several orders in magnitude smaller than those produced using conventional spinning techniques. By optimizing parameters such as: i) the intrinsic properties of the solution including the polarity and surface tension of the solvent, the molecular weight and conformation of the polymer chain, and the viscosity, elasticity, and electrical conductivity of the solution; and the operational conditions such as the strength of electric field, the distance between spinneret and collector, and the feeding rate of the solution, electrospinning is capable of generating fibers as thin as tens of nanometers in diameter. Additional parameters that affect the properties of electrospun fiber include the molecular weight, molecular-weight distribution and structure (branched, linear etc.) of the polymer, solution properties (viscosity, conductivity and surface tension), electric potential, flow rate and concentration, distance between the capillary and collection screen, ambient parameters (temperature, humidity and air velocity in the chamber), motion of target screen (collector) and so forth. Fabrication of highly porous fibers may be achieved by electrospinning the jet directly into a cryogenic liquid. Well-defined pores developed on the surface of each fiber as a result of temperature-induced phase separation between the polymer and the solvent and the evaporation of solvent under a freeze-drying condition.

Several approaches have been developed to organize electrospun fibers into aligned arrays. For example, electrospun fibers can be aligned into a uniaxial array by replacing the single-piece collector with a pair of conductive substrates separated by a void gap. In this case, the nanofibers tend to be stretched across the gap oriented perpendicular to the edges of the electrodes. It was also shown that the paired electrodes could be patterned on an insulating substrate such as quartz or polystyrene so the uniaxially aligned fibers could be stacked layer-by-layer into a 3D lattice. By controlling the electrode pattern and/or the sequence for applying high voltage, it is also possible to generate more complex architectures consisting of well-aligned nanofibers.

Electrospun nanofibers could also be directly deposited on various objects to obtain nanofiber-based constructs with well-defined and controllable shapes. In addition, one can manually process membranes of aligned or randomly oriented nanofibers into various types of constructs after electrospinning: for example, fabrication of a tube by rolling up a fibrous membrane or the preparation of discs with controllable diameters by punching a fibrous membrane.

The present invention relates to any eletrospinning technique known in the art, which includes *Electrospinning*, J. Stanger, N. Tucker, and M. Staiger, I-Smithers Rapra publishing (UK), *An Introduction to Electrospinning and Nanofibers*, S. Ramakrishna, K. Fujihara, W-E Teo, World Scientific Publishing Co. Pte Ltd (June 2005), *Electrospinning of micro- and nanofibers: fundamentals and applications in separation and filtration processes*, Y. Fillatov, A. Budyka, and V. Kirichenko (Trans. D. Letterman), Begell House Inc., New York, USA, 2007, which are all incorporated herein by reference in their entirety.

Suitable electrospinning techniques are disclosed, e.g., in International Patent Application, Publication Nos. WO 2002/049535, WO 2002/049536, WO 2002/049536, WO 2002/049678, WO 2002/074189, WO 2002/074190, WO 2002/074191, WO 2005/032400 and WO 2005/065578, the contents of which are hereby incorporated by reference. It is to be understood that although the according to the presently preferred embodiment of the invention is described with a particular emphasis to the electrospinning technique, it is not intended to limit the scope of the invention to the electrospinning technique. Representative examples of other spinning techniques suitable for the present embodiments include, without limitation, a wet spinning technique, a dry spinning technique, a gel spinning technique, a dispersion spinning technique, a reaction spinning technique or a tack spinning technique. Such and other spinning techniques are known in the art and disclosed, e.g., in U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference.

In further embodiments of a device of the invention, said swellable polymer fibrous material comprise water-swellable polymer fibrous material.

In other embodiments of a device of the invention, said non-woven swellable polymeric fibrous material is characterized by swellability of at least 50 percent of said fibrous material volume. In further embodiments, said swellability is in the range of about 50 to 250 percent of said fibrous material volume (i.e. about 50, 60, 70, 80, 90, 100, 110, 120, 130, 140, 150, 160, 170, 180, 190, 200, 210, 220, 230, 240, 250 percent).

In further embodiments of a device of the invention, said non-woven swellable polymeric fibrous material is characterized by elasticity of at least 10 percent. In some further embodiments said elasticity is in the range of between about 10 to about 50 percent (i.e. about 10, 15, 20, 25, 30, 35, 40, 45 and 50 percent).

In further embodiments of a device of the invention, said porous swellable polymeric fibrous material is characterized by porosity of at least 50 percent. In some embodiments said porosity is between about 50 to about 95 percent (i.e. about 50, 55, 60, 65, 70, 75, 80, 85, 90 and 95 percent).

In further embodiments of a device of the invention, said porous swellable polymeric fibrous material is characterized by having a pore size larger than possible intraocular cellular debris. In further embodiments of a device of the invention, said porous swellable polymeric fibrous material is characterized by having a pore size of between about 15 μm to 150 μm (i.e. about 15, 20, 25, 30, 35, 40, 45, 50, 55, 60, 65, 70, 75, 80, 85, 90, 95, 100, 110, 120, 130, 140, 150 μm).

In further embodiments of a device of the invention, said porous swellable polymeric fibrous material is characterized by water permeability of at least 0.3 ml/cm2/min. In some embodiments, permeability is between about 0.3 to about 10 ml/cm2/min (i.e. 0.3, 0.4, 0.5, 0.6, 0.7, 0.8, 0.9, 1, 2, 3, 4, 5, 6, 7, 8, 9, 10 ml/cm$^2$/min).

In further embodiments, a device of the invention comprises at least two types of porous swellable polymeric fibrous material arranged in a layered structure.

In other embodiments, said device of the invention further comprises at least one pharmaceutical agent incorporated in said porous swellable polymeric fibrous material and/or said external enveloping layer. In some embodiments said at least one pharmaceutical agent is selected from an antifibrotic agent, an anticoagulant, an antithrombotic agent, an antibiotic agent, an anti-inflammatory agent, a biodegradable material, a pressure lowering agent, an antiangiogenic agent, or any combination thereof. Non-limiting examples of agents suitable to be incorporated in a device of the invention include mitomycin C, 5-fluoro uracil, heparin, steroidal and/or non steroidal anti inflammatory, bevacizumab/ranibizumab, beta blocker agents, alpha agonist agents, carbonic anhydrase inhibitors, prostaglandin analogs and any combination thereof.

In some embodiments, said at least one pharmaceutical agent is deposited/coated on the external surface of said fibrous material of a device of the invention. In other embodiments said at least one pharmaceutical agent is incorporated within the fibrous material of a device of the invention (i.e. in between the plurality of fibers of said material). In further embodiments, said at least one pharmaceutical agent are formulated to provide an immediate (postoperative) release or in a sustained/controlled release profile.

In further embodiments a device of the invention has an external (enveloping) at least one layer of at least one different type of polymeric fibrous material. Under further embodiments, said external (enveloping) at least one layer is biostable and/or biocompatible polymer.

In further embodiments, said external (enveloping) at least one layer is made of a biodegradable polymer. In further embodiments, said external (enveloping) layer has an elongated shape exceeding the length of said swellable polymeric fibrous material.

In yet further embodiments of the invention, said porous swellable fibrous polymeric material is inserted within an external tubular structure. In some embodiments said external tubular structure is formed from a biocompatible material. In other embodiments said tubular structure is formed from a biodegradable material.

In further embodiments said tubular structure is reinforced at its parameter (internal or external) with a reinforcing coil (in some embodiments a metal, alloy or polymeric coil), capable of retaining the tubular structure and avoiding any collapse or possible blockage of the device.

In a further aspect the invention provides a device of the invention, implanted through the sclera and allowing drainage of aqueous humor to the intra-orbital space.

In another one of its aspects the preset invention provides a surgical method for implanting a device of the invention into the eye of a subject, said method comprising:

Performing a localized peritomy comprising removing conjunctiva and tenon capsule;

Creating a trans-scleral tubular channel; in some embodiments said tubular channel is created by means of a sharp cylindrical knife;

Locating said device into said tubular channel wherein at least one end of said device is directed towards (or located at) the anterior chamber and its opposite end is directed towards (or located at) the orbital space.

In a further one of its aspects the invention provides a device comprising a tubular portion having a first and second opening, being implanted so that first opening is located in the anterior chamber and second opening is located at the intra or extraconal orbital space and said tubular portion is located on the sclera.

The invention further provides a method of draining aqueous humor from the anterior chamber to the intra-orbital space comprising the step of implanting a device comprising a tubular portion having a first and second opening; wherein said first opening is located in the anterior chamber and second opening is located at the intra or extra-orbital space and said tubular portion is located on the sclera.

FIG. 1 represents a schematic illustration of the eyeball in a transverse plane through the eyeball, wherein it is illustrated that a device of the invention 100 is located between the anterior chamber 101 and the orbital space 102, thus directing the outflow of fluid accumulated at the anterior chamber 101 towards the orbital space of the eye. The surgical method of the invention for implanting a device of the invention involves localized peritomy comprising removing conjunctiva 103 and tenon capsule (not shown), creating a trans-scleral (sclera indicated as 104) tubular channel 105 wherein said device 100 is located thereafter.

Figure 2:
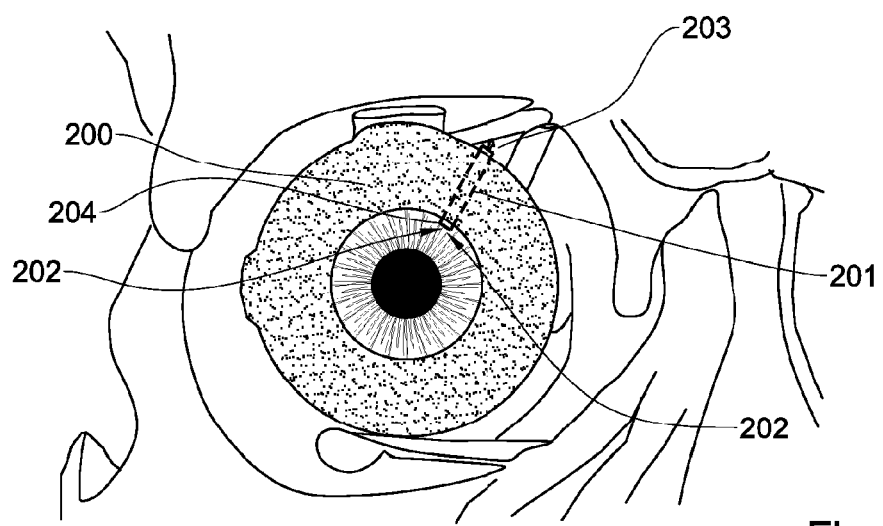
FIG. 2 represents a schematic illustration of the frontal view of the eyeball, wherein the procedure for implanting a device of the invention is indicated.

FIG. 2 represents a schematic illustration of the frontal view of the eyeball, wherein dotted line 200 represents the peritomy cut (only on limbus) of the conjunctiva and tenon capsule (not shown) and the dotted line 201 represents the sub-conjunctival space wherein a device of the invention is located, in which one end 204 is directed towards the anterior chamber (not shown) and its opposite end is located towards the orbital space 203. The direction of the outflow is represented by arrows 202.

Figure 3:
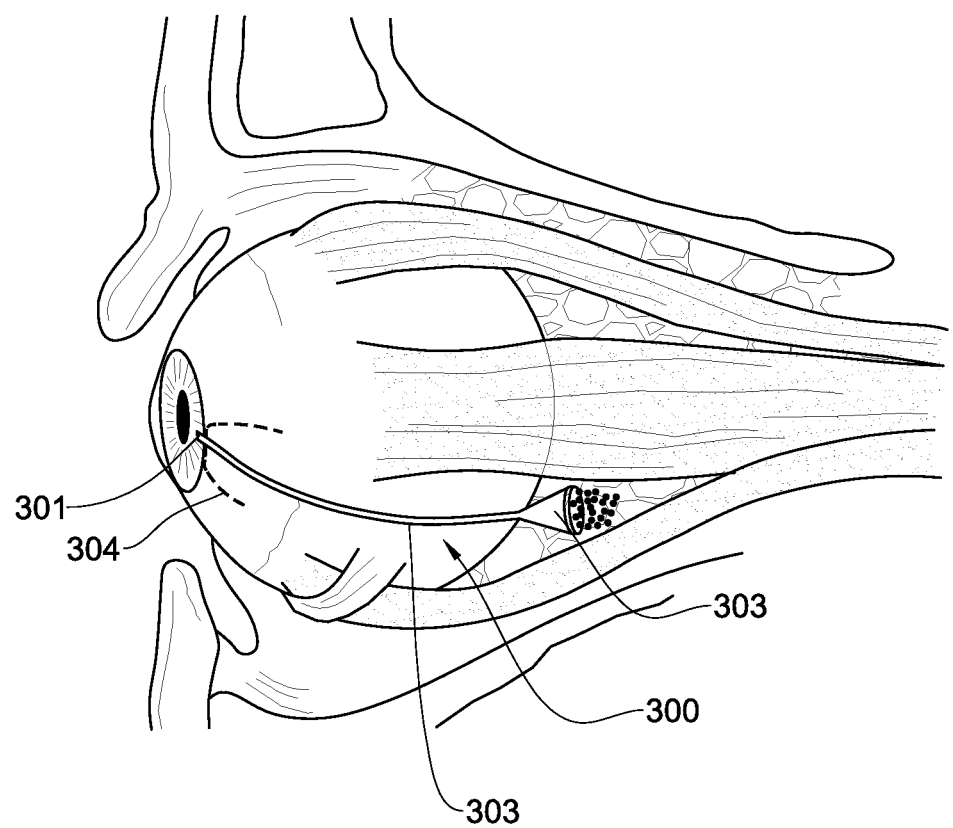
FIG. 3 represents a schematic illustration of the eyeball wherein the location of the device of the invention upon its implanting is indicated.

FIG. 3 shows a device of the invention 300, having a first opening 301 located at the anterior chamber and a second opening 302 located at the intra orbital space (intraconal space, but could also end at the extraconal space as well), and a tubular portion 303 going underneath the conjunctiva. Dotted line, 304, marks the peritomy. Accumulated liquid in the anterior chamber of the glaucomatic eye exits through the first opening 301 of the device of the invention and is evacuated to the intraconal space through the tubular portion 303 to the second opening 302.

It is noted that a device of the invention enables the performance of the above simplified surgical procedure, allowing a quick learning curve to the surgeon performing said procedure and method of implanting said device of the invention, less side effects including exposure of tubular element, late onset infection, early and late hypotony and physiological intraocular pressure. Due to the specified characteristic features of the device of the invention no surge of outflow fluid is detectable. It is noted that the gold standard of surgical glaucoma relief is trabeculectomy operation including iridectomy (not to block the outflow due surge flow of fluid). This complicated procedure is avoided using a device of the invention.

In a further aspect the invention provides a method for controlling the liquid outflow from the anterior chamber of the eye comprising: providing a device of the invention and implanting said device into the eye of a subject so that at least one end of said device is directed towards (or located at) the anterior chamber and its opposite end is directed towards (or located at) the orbital space; thereby controlling the outflow of liquid from the anterior chamber of the eye.

In some embodiments, the implanting of said device in the eye of a subject in need thereof is conducted by:

Performing a localized peritomy comprising removing conjunctiva and tenon capsule;

Creating a trans-scleral tubular channel; in some embodiments said tubular channel is created by means of a sharp cylindrical knife;

Locating said device into said tubular channel wherein at least one end of said device is directed towards (or located at) the anterior chamber and its opposite end is directed towards (or located at) the orbital space.

In some embodiments of a method of the invention said location of a device of the invention into said tubular channel is conducted by advancing an insertion apparatus engaged with a device of the invention; disengaging said insertion apparatus while securing said device in a location of the eye wherein liquid from said anterior chamber flows out from said chamber in a controlled manner.

In some embodiments of a surgical method of the invention the internal ostium of said trans-scleral tubular channel is located either in the anterior chamber angle or intravitrealy.

In further embodiments of a surgical method of the invention said device of the invention is located so that at least one end of said device is positioned intraocularly and its opposite end is positioned intraorbitaly.

In other embodiments of a surgical method of the invention said device of the invention is secured to adjacent sclera. Under such embodiments of a method of the invention, securing overlying conjunctiva and tenon does not expose the sclera and/or the device.

In further embodiments of a surgical method of the invention, at least one antifibrotic agent is administered in situ prior to or subsequent to any step of said method.

The invention claimed is:

1. An implantable device for controlling liquid outflow from an anterior chamber of an eye, comprising:
    an implantable elongate body having a first end that is positionable at an anterior chamber of the eye and a second end that is positionable at a conal orbital space of the eye,
    wherein the elongate body is positionable on the sclera of the eye and is configured to provide a fluid path for draining fluid entering the first end of the elongate body from the anterior chamber to the conal orbital space via the second end,
    wherein the elongate body comprises at least one first porous swellable polymeric fibrous material and at least one external tubular structure, the at least one first porous swellable fibrous polymeric material being disposed within the at least one external tubular structure.

2. The device according to claim 1, wherein said first porous swellable polymeric fibrous material is non-woven.

3. The device according to claim 1, wherein said first porous swellable polymeric fibrous material is electrospun.

4. The device according to claim 1, having an external at least one layer including at least one second polymeric fibrous material.

5. The device according to claim 1, having an external at least one layer including at least one second polymeric fibrous material wherein said at least one second polymeric fibrous material is a biostable and/or a biocompatible polymer.

6. The device according to claim 1, having an external at least one layer including at least one second polymeric fibrous material wherein said external at least one layer is made of a biodegradable polymer.

7. The device according to claim 1, having an external at least one layer including at least one second polymeric fibrous material wherein said external layer has an elongated shape exceeding the length of said first porous swellable polymeric fibrous material.

8. The device according to claim 1, wherein said first porous swellable polymer fibrous material comprises a water-swellable polymer fibrous material.

9. The device according to claim 1, wherein said first porous swellable polymeric fibrous material is non-woven and has a swellability of at least 50 percent in volume.

10. The device according to claim 1, wherein said first porous swellable polymeric fibrous material is non-woven and has an elasticity of at least 10 percent.

11. The device according to claim 1, wherein said first porous swellable polymeric fibrous material has a porosity of at least 50 percent.

12. The device according to claim 1, wherein said first porous swellable polymeric fibrous material has a water permeability of at least 0.3 ml/cm$^2$/min.

13. The device according to claim 1, comprising at least two first porous swellable polymeric fibrous materials arranged in a layered structure.

14. The device according to claim 1, further comprising at least one pharmaceutical agent incorporated in said first porous swellable polymeric fibrous material.

15. The device according to claim 14, wherein said at least one pharmaceutical agent comprises an antifibrotic agent, an anticoagulant, an antithrombotic agent, an antibiotic agent, an anti-inflammatory agent, a biodegradable material, a pressure lowering agent, an antiangiogenic agent or any combination thereof.

16. A method for controlling the liquid outflow from the anterior chamber of the eye comprising:

providing a device according to claim 1; and implanting said device into the eye of a subject so that at least one end of said device is directed towards (or located at) the anterior chamber and its opposite end is directed towards (or located at) the orbital space.

17. The implantable device of claim 1, wherein the first porous swellable polymeric fibrous material comprises pores which increase in volume responsive to an increase of intraocular pressure of fluid at the anterior chamber of the eye for adjusting intraocular pressure in the eye.

18. An implantable device for controlling liquid outflow from an anterior chamber of an eye, comprising: an implantable elongate body having a first end that is positionable at an anterior chamber of an eye and a second end that is positionable at a conal orbital space of the eye, wherein the elongate body is positionable on the sclera of the eye and is configured to provide a fluid path for draining fluid entering the first end of the elongate body from the anterior chamber to the conal orbital space via the second end, wherein the elongate body comprises at least one first porous swellable polymeric fibrous material and at least one external tubular structure.

19. An implantable device for controlling and maintaining the dynamic equilibrium of aqueous production and liquid outflow from an anterior chamber of an eye, comprising: an implantable elongate body having a first end that is positionable at an anterior chamber of an eye and a second end that is positionable at a conal orbital space of the eye, wherein the elongate body is positionable on the sclera of the eye and is configured to provide a fluid path for draining fluid entering the first end of the elongate body from the anterior chamber to the conal orbital space via the second end, wherein the elongate body comprises at least one first porous swellable polymeric fibrous material and at least one external tubular structure.

* * * * *